US007066982B2

(12) United States Patent
Ma et al.

(10) Patent No.: US 7,066,982 B2
(45) Date of Patent: *Jun. 27, 2006

(54) CONTAMINANT REMOVAL BY FERNS VIA FOLIAR-APPLICATION AND EXCISED/GROUND FRONDS

(75) Inventors: Lena Q. Ma, Gainesville, FL (US); Mike Shuxin Tu, Wuhan (CN); Abioye O. Fayiga, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 75 days.

This patent is subject to a terminal disclaimer.

(21) Appl. No.: 10/825,993

(22) Filed: Apr. 16, 2004

(65) Prior Publication Data

US 2004/0197812 A1 Oct. 7, 2004

Related U.S. Application Data

(60) Continuation-in-part of application No. 10/756,237, filed on Jan. 12, 2004, which is a continuation-in-part of application No. 09/948,969, filed on Sep. 7, 2001, now abandoned, which is a division of application No. 09/546,941, filed on Apr. 11, 2000, now Pat. No. 6,302,942, which is a continuation-in-part of application No. 09/471,566, filed on Dec. 23, 1999, now Pat. No. 6,280,500.

(60) Provisional application No. 60/129,203, filed on Apr. 14, 1999.

(51) Int. Cl.
*C22B 3/18* (2006.01)
*C22B 3/24* (2006.01)

(52) U.S. Cl. ............................ 75/711; 75/710; 75/712; 210/602; 210/681; 47/58.1; 800/298; 800/295

(58) Field of Classification Search ................ 75/711, 75/712, 710; 210/602, 682; 47/58.1; 800/298
See application file for complete search history.

(56) References Cited

U.S. PATENT DOCUMENTS

| | | | |
|---|---|---|---|
| 5,000,852 A * | 3/1991 | Tel-Or et al. ................ | 210/602 |
| 5,364,451 A | 11/1994 | Raskin et al. ................ | 75/710 |
| 5,785,735 A * | 7/1998 | Raskin et al. ................ | 75/711 |
| 5,809,693 A * | 9/1998 | Chet et al. ................... | 47/58 |
| 5,917,117 A | 6/1999 | Ensley et al. ................ | 75/722 |
| 5,927,005 A | 7/1999 | Gardea-Torresdey et al. ........... | 47/58.1 |
| 5,944,872 A | 8/1999 | Chaney et al. ................ | 75/712 |
| 6,005,092 A | 12/1999 | Shoseyov et al. ........... | 536/23.6 |
| 6,280,500 B1 * | 8/2001 | Ma et al. ..................... | 75/711 |
| 6,302,942 B1 * | 10/2001 | Ma et al. ..................... | 75/712 |

OTHER PUBLICATIONS

Ho. et al. Bull. Environ. Contam. Toxi. vol. 35, pp. 430-438 (1985).*
Ho et al. Bull Environ. Contam. Toxicol. vol. 35, pp. 430-438, 1985.*
Noctor et al. Journal of Experimental Botany, vol. 49, No. 321, pp. 623-647, Apr. 1998.*
Bennett, F.A., E.K. Tyler, R.R. Brooks, P.E.H. Gregg, and R.B. Stewart (1998). Fertilisation of Hyperaccumulator to Enhance their Potential for Phytoremediation and Phytomining. *Plants that Hyperaccumulate Heavy Metals*. R.R. Brooks. New York, CAB International: 249-259.
Cullen, W.R. and K.J. Reimer (1989). "Arsenic Speciation in the Environment." *Chem. Rev.*(89): 713-764.
Cunningham, S.D., J.R. Shann. D.E. Crowley, and T.A. Anderson (1997). Phytoremediation of Contaminated Water and Soil. *Phytoremediation of Soil and Water Contaminants*. E.L. Kruger, T.A. Anderson and J.R. Coars. Washington, DC, American Chemical Society: 2-15.
Dix, M.E., N.B. Klopfenstein, J.W. Zhang, S.W. Workman, and M.S. Kim (1997). Potential Use of Populus for Phytoremediation of Enviromental Pollution in Riparian Zones.
Ebbs, S.D., M.M. Lasat, D.I. Brady, J. Cornish. R. Gordan, and L.V. Kochian (1997). "Phytoextraction of Cadmium and Zinc from a Contaminated Soil." *Journal of Environmental Quality* 26:1424-1430.
Fowler, B.A. (1977). Toxicology of Environmental Arsenic. *Toxicology of Trace Elements*. R.A. Goyer and M.A. Mehlman. New York, NY, Hemisphere Publishing corperation. 2: 79-122.
Grant. C. and A.J. Dobbs (1977). "The Growth and Metal Content of Plants Grown in Soil Contaminated by a Copper/Chrome/Arsenic Wood Preservative." *Environ. Pollut* 14: 213-226.

(Continued)

*Primary Examiner*—Medina A. Ibrahim
(74) *Attorney, Agent, or Firm*—Brian S. Steinberger; Law Offices Of Brian S. Steinberger, P.A.

(57) ABSTRACT

Processes, methods, materials and compositions for phytoremediating contaminated waters, which have been contaminated with pollutants such as arsenic, phosphorous, or other metals. Fern plants can be used to accumulate pollutants from contaminated water, including aqueous solution, waste water, ground water, surface water, combinations thereof. Pollutants and contaminants can be removed from the water, soil and wetland type environment via foliar application, excised leaflets, and/or through compositions of ground leaflets. The biomass can be harvested and readily disposed of, or can be treated to recover the pollutants and contaminants.

51 Claims, No Drawings

OTHER PUBLICATIONS

Huang, J.W., M.J. Blaylock, Y. Kapulnik, and B.D. Easley (1998). "Phytoremediation of Uranium—Contaminated Soils: Role of Organic Acids in Triggering Uranium Hyperaccumulation in Plants." *Environ. Sci. Technol.* . 32: 2004-2008.

Kramer, U., R.D. Smith. W. Wenzel. I. Raskin, and D.E. Salt (1997). "The Role of Metal Transport and Tolerance in Nickel Hyperaccumulation by Thaspi goesingense Halaesy. " *Plant Physiol,* (115): 1641-1650.

Lasat, M. M., M. Furmann, S. D. Ebbs, j. E. Cornish, and L.V. Kochian (1998). "Phytoremediation of a Radiocesium—Contaminated Soil: Evaluation of Cesion-137 bioaccumulation in the Shots of Three Plant Species." *Journal of Envirnomental Quality* 27 165-196.

Ma, L. Q., F. Tan, and W. H. Harris, 1997. Concentration and distribution of 11 elements in Flordia soils. J. Environ. Qual. 26: 769-775.

McGrath, S. P. (1998). Phytoextraction for Soil Remediation. *Plants that Hyperaccumulate Heavy Metals*. R. R. Books. New York, NY, CAB International: 261-287.

Porter, E. K. and P. J. Peterson (1977). Arsenic Tolerance in Grasses Growing on Mine Waste. *Environ. Pollut* 14: 255-265.

Squibb, K.S. and B.A. Fowler (1983). The Toxicity of Arsenic and its Compounds. *Biological and Environmental Effects of Arsenic*. B.A. Fowler. Research Triangle Park, NC, Elsevier Science Publishers: 233-269.

Walsh, L.M. and D.R. Keeney (1975). Behavior and Phytotoxicity of Inorganic Arsenicals in Soils. *Arsenical Pesticides*. E. A. Woolson. Washington, D.C., ACS: 35-52.

Blaylock, et al., Enhanced Accumulation of PH in Indian Mustard by Soil-Applied Chelating Agents, *Environ. Sci Technol.* 1997, 31. p. 860-865.

Pickering, et al., Reduction and Coordination of Arsenic in Indian Mustard, *Plant Physiology*. Apr. 2000, vol. 122, p. 1171-1177.

Noctor, et al., Glutathione: Biosynthesis, Metabolism and Relationship to Stress Tolerance Explored in Transformed Plants, *Journal of Experimental Botany*, vol. 49 No. 321. p. 623-647. Apr. 1998.

Ho, et al., Potential Use of A Roadside Fern (*Pteris Vittata*) to Biomonitor Pb and Other Aerial Metal Deposition, *Bull. Environ. Contam. Toxicol* . (1985) 35:430-438.

* cited by examiner

CONTAMINANT REMOVAL BY FERNS VIA FOLIAR-APPLICATION AND EXCISED/GROUND FRONDS

This invention is a Continuation-In-Part (CIP) of U.S. Ser. No. 10/756,237 filed Jan. 12, 2004, which is a Continuation-In-Part (CIP) of U.S. Ser. No. 09/948,969, filed Sep. 7, 2001 now abandoned, which is a Divisional Application of U.S. Ser. No. 09/546,941 filed Apr. 11, 2000, now U.S. Pat. No. 6,302,942, which is a Continuation-In-Part (CIP) of U.S. Ser. No. 09/471,566 filed Dec. 23, 1999, now U.S. Pat. No. 6,280,500, which claims the benefit of priority from U.S. Provisional Application Ser. No. 60/129,203, filed Apr. 14, 1999.

FIELD OF THE INVENTION

This invention relates to compositions and methods of phytoremediation using fern plants for removing contaminated substances such as arsenic and phosphorus, from sites containing polluted soils and waters and airborne substances such as those found with waste water, ground water, surface water, combinations thereof via foliar application and excised and ground plant parts.

BACKGROUND OF THE INVENTION

Arsenic Chemistry and Toxicity

Arsenic is a major contaminant of soils, sediments, wastes, and water in the United States and in foreign countries. Contamination of soils results from, for example, pesticides application and pressure-treated woods. Not only is arsenic a prevalent contaminant but it is also particularly dangerous because it is a known carcinogen. Currently there is no cost effective and efficient way to clean up sites contaminated with arsenic.

The use of arsenic in agricultural and industrial processes has resulted in numerous contaminated sites in Florida. During the early part of the $20^{th}$ century, arsenic was commonly used as an insecticide component to control disease-carrying ticks on southern cattle so that Florida cattlemen could sell to the northern cattle markets. Arsenic, typically in the form of arsenic pentoxide, was also used in conjunction with copper sulfate and sodium or potassium dichromate as a wood preservative which is known as the copper/chromium/arsenic wood preservative process (CCA). With both of these processes, the risk of soil contamination from spills and leaks was great. The arsenic level at many of these sites is currently higher than 600 mg/kg even after years of idleness. The typical concentration range in soil is between 0.1 to 40 mg/kg, with a mean concentration of 5–6 mg/kg. The typical range of arsenic in Florida soils is 0.01 to 50.6 mg/kg.

In most soil systems, arsenic is present in many forms of which arsenate is typically the dominant one. In this form, it has properties very similar to phosphate including the formation of insoluble salts with cations and sorption by soil constituents. Because arsenic has a wide range of oxidation states (−3, 0, +3, and +5) it has the ability to form many types of organic and inorganic complexes. At high pH ranges, typically 7 to 9, the arsenic in soils predominantly consists of complex oxyanions of As(V), such as $AsO_2^{-1}$, $AsO_4^{-3}$, $HAsO_4^{-2}$, and $H_2AsO_4^{-1}$. In soils with low pH and low Eh, the predominant forms of arsenic are the arsenite ($H_3AsO_3$).

Although arsenic is commonly found in all natural systems at minute levels, it can be very toxic to both plants and animals at higher concentrations. The toxic effects of arsenic have been known for some time. The exposure of animals to arsenic is second in toxicity only to lead (Pb) for many farm and household animals. Most cases of arsenic poisoning in animals occur in bovine and feline species as a result of contaminated feed supplies. Other species that are affected are forage-eating animals, such as horses and sheep, that encounter fields that may have been treated with arsenic pesticides. The toxic effects of arsenic to humans and animals can be related to the interactions that occur within the cells of poisoned individuals, especially the mitochondria.

Phytoextraction

Arsenic contamination in the environment is of concern due to its biological activities as a teratogen, carcinogen, and mutagen as well as its detrimental effects on the immune system. Due to the concern expressed over arsenic contaminated sites, various remediation techniques have been developed. Methods for remediating arsenic contaminated sites can be performed in situ and ex situ and have varying degrees of complexity, effectiveness, and cost. Due to the lack of effective technologies and the costs associated with the excavation and landfilling of the soil materials, efforts to remediate these arsenic contaminated sites have been minimal. These remediation methods can be divided into three groups: chemical, physical, and biological remediation methods.

One of the biological remediation techniques is phytoremediation, more specifically phytoextraction. Phytoextraction attempts to remove contaminants from the rhizosphere through plant uptake and the contaminants are accumulated in roots, leaves and/or stems. The plant materials are then harvested and the contaminants reclaimed from the plant biomass or the materials are disposed of at a hazardous waste facility. Phytoextraction is an organic, low input, and solar energy powered remediation technique that is applicable to sites with surface and low to medium levels of contamination. The ideal plant for phytoextraction must be able to tolerate high levels of the element in root and shoot cells. Plants used for phytoextraction must have the ability to translocate the contaminant from roots to shoots at high rates. For most plants, root concentrations are much higher than shoot concentrations, but in hyperaccumulators, shoot metal concentrations exceed root.

There have been several reports of arsenic accumulating plants; on mine wastes from various sites in the United Kingdom; on smelter wastes in northeast Portugal and near a copper mine site in northern Peru. Porter and Peterson (1975) reported that *Jasione montana, Calluna vulgaris, Agrostis tenuis* and *Agrostis stolonifera* collected from highly arsenic polluted sites in the UK contained 6640, 4130, 3470 and 1350 µg As $g^{-1}$ dry mass, respectively. De Koe (1994) found *Agrostis castellana* from the gold mines in Portugal reached arsenic values of 1900 mg $kg^{-1}$ but was still in the range reported by Porter and Peterson (1975) for other *Agrostis* species. The highest As concentration previously reported in plants was for the grass *Paspalum racemosum*, which contained up to 5,280 µg As $g^{-1}$ in their dead leaves.

Currently, many plants have been identified that can be utilized to remediate soil and water systems contaminated with metals, metalloids, petroleum constituents, pesticides, and industrial wastes. Also, many plant species have been identified that accumulate lead, selenium, nickel, zinc, and other metals. For example, U.S. Pat. Nos. 5,364,451 and 5,711,784 describe phytoremediation of metal-contaminated soils. For the remediation of contaminated sites contaminated with metals, phytoextraction can be an attractive option. Phytoextraction is the process of removing a contaminant from a system via plant roots for remediation purposes.

*Pteris vittata*

There are more than 400 hyperaccumulators identified in different taxa mostly belong to nickel, cadmium, and zinc (Brooks, 1998). Recently, Ma et al. (2001) discovered the first known vascular plant, a fern, (*Pteris vittata* L.), commonly known as Chinese brake fern that hyperaccumulates arsenic. *Pteris vittata* took up phenomenal concentrations of arsenic (as high as 2.3%) from soil and allocated most of it to the aboveground fronds (up to 90%) for final storage (Tu and Ma, 2002). Most importantly, the hyperaccumulation of arsenic was accompanied by an increased biomass of the aboveground plant parts (Ma et al., 2001; Tu and Ma, 2002). Other desirable characters permitting *P. vittata* as an ideal plant for phytoremediation include its perennial growth habit, disease and pest resistance, fast vigorous growth, and diverse ecological niche with high pH.

Arsenic hyperaccumulation largely depends on the root geometry and morphology since root systems that have higher ratios of surface area to volume will more effectively explore a larger volume of soil. *Pteris vittata* develops an extensive network of root system enriched with root hairs. Bondada and Ma (2002) reported the root length and density of the fern grown in arsenic contaminated soil were 363 $\mu m$ and 9 $\mu m^{-2}$, substantially greater than the length and density of *P. vittata* grown in cadmium contaminated media (Gupta and Devi, 1994) indicating that arsenic may have stimulatory effect of root hair development in the fern. Since hyperaccumulation of metals appears to be driven by increased rates of root uptake, the dense population of root hairs in the fern, in addition to increasing absorptive surface, may contribute to increased rates of arsenic uptake by increasing number of transporters per gram fresh weight. Even though significant progress has been made in understanding the physiological basis of plant tolerance to arsenic, there remains considerable uncertainty about the mechanism in *P. vittata*. Tu et al. (2002) reported that *P. vittata* roots with low arsenic concentration and high phosphorus: arsenic ratio exhibited increased affinity to, and high influx rate of arsenic.

*Pteris vittata* has the remarkable ability to hyperaccumulate arsenic in the fronds, with frond concentrations reaching levels up to 100 fold greater than soil concentrations. This ratio is held both for uncontaminated (6 mg $kg^{-1}$ As) and highly contaminated (1,500 mg $kg^{-1}$ As) soils. The fern is capable of taking up of a range of inorganic and organic arsenic species including arsenate, arsenite and MMA. In the fern, arsenic is mostly present in inorganic forms, with 47–80% of the arsenic present as arsenite in the fronds.

Arsenic Uptake other than Roots

Studies dealing with uptake of heavy metals by hyperaccumulators focused primarily on metal uptake from the soil solution via the root system. This is because most of the heavy metals reside in the soil system, and after uptake, they are often confined in the roots. Other than the roots, the aerial organs such as leaves are also capable of absorbing soluble heavy metals if they receive it in aqueous form (Lepp, 1975). Metals such as Cd, Zn, Cu, and Pb enter the leaf through foliar pathways, however, their entry through the leaf cuticle into leaf varied depending upon metal species (Little and Martin, 1972; Greger et al., 1993).

Arsenic, a highly soluble metalloid, is normally applied in combination with other compounds as a toxin for pest mortality (Handson, 1984). In the past, however, foliar sprays of arsenic had been used to improve juice quality in citrus (Procopiou and Wallace, 1979) indicating that arsenic could gain entry into the plants through the foliar pathways.

Since different biochemical reactions occur in different parts of a plant, excised plant, such as shoots, stems, leaves and roots, have been widely used to characterize the absorption and metabolism of nutrients and chemicals as well as heavy metals in plants (Facanha and Okorokova-Facanha, 2002; Waldrop et al., 1996; Zhang and Taylor, 1991). We have examined the uptake of different As species (organic/inorganic and arsenate/arsenite) by *P. vittata* and As speciation in its plant biomass (Ma et al., 2001; Tu and Ma, 2002). However, there are many questions remain unanswered, such as where As reduction occurs in the plant, i.e. roots, fronds or both, and how P affects plant As uptake and reduction. The hypotheses were that both P and As species could affect plant As uptake, speciation and thiol formation in *P. vittata*, and such effects could be effectively characterized by use of excised parts of *P. vittata*. It was expected that use of excised parts of *P. vittata* to characterize As uptake, speciation and thiol formation would shed light on its mechanisms of As hyperaccumulation.

Although live biological systems work well for low concentrations, they cannot survive the high levels that are found in heavily contaminated areas and industrial effluents. The use of non-living biomaterial containing metal-binding compounds would have the advantage of not requiring care and maintenance as well as being useful in remediating areas with high levels of contaminants that would otherwise kill live systems. A wide variety of biomass, including bacteria, fungi, algae and higher plants have been tested as adsorbents to clean up metals in contaminated aqueous environments. Live or dead cultured cells of a higher plant, *Datura innoxia* Mill have been used to remove $Ba^{2+}$ from solution. Aquatic ferns, *Azolla filiculoides* Lam and *Azolla pinnata* R.Br have also been reported to accumulate metals and can be used as biosorbents in remediating industrial effluents. A large number of aquatic plants were reported to be utilized for water purification and removing heavy metals from water. However, in aquatic plants, characterized by small size and slow growing roots, the efficiency of metal removal seems to be low. High water content in these plants renders their drying, composting and incineration processes complicated.

Terrestrial plants develop longer, fibrous root systems with root hairs, which creates a high surface area for effective absorption, concentration or precipitation of toxic metals from polluted media. An assessment of removal of toxic metals from solution by phytomass of *Quercus ilex* for a wide range of metals such as Cr, Ni, Cu, Cd and Pb indicated high sorption capacity of the phytomass for Ni and potential use as a biosorpent agent in contaminated aqueous media.

Prior to the subject invention, there has been no plant species identified that can enrich large quantities of arsenic into its biomass from contaminated soils, with arsenic concentration in plant being much greater than that in the soil. Also, prior to the subject invention there has been no report of the use of fern plants in phytoremediation. In addition, prior to the subject invention there has been no report of fern-based phytoremediation using the following methods: e.g. foliar application, excised plant parts and dry or fresh plant biomass.

SUMMARY OF THE INVENTION

A primary objective of the subject invention is to provide for compositions and methods of using fern plants for removing pollutants and contaminants such as arsenic, from water type environments.

A secondary objective of the subject invention is to provide for using fronds of fern plants to remove pollutants and contaminants by foliar application, where the pollutants/contaminants are removed through surface applications on the fronds of the fern plants.

A third objective of the subject invention is to provide for using excised portions of fern plants such as excised leaflets to remove pollutants and contaminants by placing the excised portions in contact with the pollutants and contaminants.

A fourth objective of the subject invention is to provide for using ground portions of fern plants such as ground leaflets, to remove pollutants and contaminants by mixing the resultant ground up portions into contact with the pollutants and contaminants.

The subject invention pertains to the identification of fern plants, which are able to extract pollutants from contaminated materials. In a preferred embodiment, the pollutant is arsenic.

Pollutants can be removed from materials including, but not limited to, soils, sediments, wastes, and water, and combinations, thereof by the plants of the subject invention which accumulate the pollutants in the biomass of the plant. This is advantageous because these plants can be used to efficiently remediate contaminated materials.

In a preferred embodiment the subject invention provides a method for phytoremediating arsenic-contaminated sites wherein arsenic accumulating fern plants remove arsenic from the contaminated materials. Specifically exemplified herein is the use of *Pteris vittata* (Chinese Brake fern).

The fern plants of the subject invention accumulate arsenic in very high concentrations. The plant leaves, stems, and/or roots can then be harvested and readily disposed of, thereby reducing the arsenic content of the contaminated site. Alternatively, arsenic may be recovered from the harvested plants.

The fern plants of the subject invention have many advantageous characteristics for use in phytoremediation. For example, these plants are extremely efficient in extracting arsenic from soils (extremely high arsenic enrichment factor), they grow in many environments, they grow quickly producing a large biomass and they reproduce easily. Also, advantageously, they are perennials which do not need to be replanted each year.

In addition to efficient root uptake, the fern plants can also be used to remediate arsenic contaminated water via foliar application (arsenic uptake through leaves in live plants). Additionally, arsenic uptake can take place in stem portions and spore(s) of the live plant.

Another embodiment includes using excised plant portions to remove pollutants and contaminants. For example, floating excised fern leaflets in water (leaflets are detached from a live plant), can remove arsenic type pollutants.

Still another embodiment includes adding ground fern biomass (fresh or dry) to contaminated sites to remove pollutants and contaminants therefrom.

Further objects and advantages of this invention will be apparent from the following detailed description of the presently preferred embodiments, a detailed description of the following examples and the accompanying drawing.

BRIEF DESCRIPTION OF THE EXAMPLES

Example 1 refers to arsenic removal by *P. vittata* and *P. cretica* Mayii from arsenic contaminated water (Tables 1 and 2).

Example 2 refers to arsenic accumulation in *P. vittata* via foliar application (Tables 3 and 4).

Example 3 refers to arsenic accumulation in *P. vittata* using excised fern leaflets (Tables 5 and 6).

Example 4 refers to arsenic accumulation in *P. vittata* using ground fern biomass (Tables 7 and 8).

DETAILED DESCRIPTION OF THE PREFERRED EMBODIMENTS

Before explaining the disclosed embodiments of the present invention in detail, it is to be understood that the invention is not limited in its application to the details of the particular arrangements shown since the invention is capable of other embodiments. Also, the terminology used herein is for the purpose of description and not of limitation.

The subject invention pertains to the identification of plants that accumulate arsenic in very high concentrations. These plants can be used to remediate arsenic contaminated sites. Preferably, the plants which are used in the remediation methods of the subject invention are fern plants. With the teachings provided herein, the person skilled in the art could, for the first time, utilize fern plants to remove various pollutants. The inorganic pollutants may be bonded to, or otherwise chemically associated with, organic or inorganic compound(s). The pollutants may be, for example, copper, chromium, or phosphorus. Preferably, arsenic is removed. The metals may be, for example, lead, gold, selenium, copper, cadmium, chromium, nickel, or zinc. Preferably, arsenic is removed. The materials from which the pollutant is removed may be any contaminated materials and can exist as liquid form, for example, surface and groundwater. The examples of waters include but not limited to groundwater, surface water, runoff, or waste water.

In a preferred embodiment, the method of the subject invention involves contacting a fern plant with arsenic-containing material and maintaining the plant in the environment under conditions sufficient for the plant to accumulate arsenic from the material. The plant is maintained in the site for a period of time and under conditions sufficient for the plant to accumulate arsenic in the stems, leaves and/or roots. The plant may be harvested from the site and disposed of.

Arsenic "accumulating" fern plants refer to the ability of the fern plants described herein to perform one, or more, of the following activities: (i) transporting arsenic from liquid into the roots and/or other tissues; (ii) physical and/or chemical sorption of arsenic to the plant biomass; and (iii) prevention or inhibition of leaching of arsenic from the contaminated material. In a preferred embodiment arsenic is transported into the leaf and/or stem tissue of the fern.

As used herein, reference to "fern plants" includes the Pteridophytes (true fern). Most fern plants are sporophytes which reproduce by means of spores. Fern plants typically produce masses of sporangia either on the underside of vegetative leaves or on specialized leaves that function only as reproductive structures. Specifically exemplified herein are fern plants of the orders Pteridales and Aspidiales and the families of Pteridaceae, Adiantaceae, Aspleniaceae, Dryopteridaceae, and Oleandraceae. Specifically exemplified genera are *Adiantum, Asparagus, Asplenium, Cyrtomium, Didymochlacna, Dyropteris, Nephrolepis, Pteridium, Rumo-*

*hra*, and *Pteris*. The *Pteris* ferns are also known as Chinese brake ferns. The specific examples of the *Pteris* ferns are *P. cretica* mayii, *P. cretica* parkerii, *P. cretica* albo-lineata, and *P. vittata*.

Fern plants useful according to the subject invention can be readily identified by those skilled in the art. Useful guides to fern plants are readily available and include, for example, Lakela, Olga and Robert W. Long: "*Ferns of Florida*", An Illustrated Manual and Identification Guide" [1976], Banyan Books, Miami, Fla.); Jones, David L. (Encyclopedia of Ferns [1987], Lothian Publishing Company PTY LTD); and Snyder, Jr., Lloyd H. and James G. Bruce (Field Guide to the Ferns and Other Pteridophytes of Georgia" [1986] The University of Georgia Press).

Advantageously, the fern plants used in the present invention: (a) can be grown to high biomass; (b) are adaptable for growth in various agro-climatic conditions; (c) are adaptable to high-density culture; (d) are amenable to genetic manipulation by crossing, selection, mutagenesis and/or gene transfer. The excellent remediation properties presented herein are under field conditions and can be improved by optimization of field conditions as described herein, or by performing the remediation process in a controlled environment such as in a greenhouse.

The conditions which can be manipulated to optimize performance in a given system include, pH, nutrients, water content, sunshine/shade, and amendments including chelators, organic amendments and inoculation of microorganisms. Optimization parameters, such as addition of nutrients (to support healthy plants) and amendments (to increase pollutant availability), apply to all fern plants, whereas others apply only to *P. vittata*. The pH may be adjusted, for example, to be greater than 6.5 using liming materials such as limestone, dolomite, hydrated lime, burn lime, alkaline industrial wastes (e.g. ash and sludge), and phosphate rock.

Essential macronutrients and micronutrients may also be applied including, for example, N, P, K, Ca, Fe, Mn, and Cu. *Pteris vittata* is a hardy plant, which shuns shade and revels in sunshine, and it requires free drainage but appreciates watering during dry periods. Additionally, chelators such as ethylene diamine tetraacetic acid (EDTA), dithylenetriaminpentaacetic acid (DTPA), nitrilotriacetic acid (NTA), citric acid, and oxalic acid can be applied. Acidic environment (pH<6) and too much salt (over fertilization) can be detrimental to fern plant growth. The fern plants specifically exemplified herein are highly useful in removing arsenic from contaminated waters.

In an alternative embodiment, the fern plants can be genetically manipulated to improve and/or expand their phytoremediation characteristics. See U.S. Pat. No. 6,005, 092 to Shoseyou et al, which is incorporated by reference. Such characteristics may be for example the growth rate of the fern plants, the uptake rate of arsenic, and the hardiness of the plant. The genetic manipulation may be through, for example, traditional breeding techniques, mutagenesis, and/or genetic engineering.

In a related embodiment, the genetic components responsible for the ability of fern plants to accumulate arsenic can be identified, isolated, and, if desired, transferred to another plant species thereby conferring on the transformed plant the ability to accumulate arsenic in useful levels. Alternatively, microorganisms and/or their genetic components involved in the arsenic removal process can be isolated and utilized.

In a specific embodiment, the subject invention provides an arsenic-accumulating fern plant. *Pteris vittata* has been shown to accumulate up to and exceeding approximately 540 mg/kg arsenic (dry weight) in its fronds. The arsenic concentrations in the water where the plant has been studied was approximately 20 mg/L. Thus, this plant has an extraordinary capability to enrich nearly approximately 27 times more arsenic in its plant tissue than in the contaminated water. Advantageously, the fern plants of the subject invention remove contaminants from water having even low concentrations of pollutants. This is important for the process of the subject invention to lower the concentration of contaminants to an acceptable level.

The preferred methods of the invention involve growing or using one or more members of these plants under conditions sufficient for them to accumulate arsenic in their biomass. The term "arsenic" also includes mixtures, or compounds, comprising arsenic and organic or inorganic compounds.

The arsenic-containing environment into which these plants are introduced is not intended to limit the scope of the invention. That is, as long as the environment can sustain growth or presence of fern plants, the environment can be purely aquatic environments (i.e., hydroponic culture). Advantageously, fern plants can be grown in the sun or in the shade, and in either moist or dry environments. For example, the subject invention may be utilized in wetlands, and the like. The pH can be as high as about 6 to about 8 or even higher.

The arsenic-accumulating fern plants suitable for the present methods extract arsenic from the environment into the biomass of the fern plant. Preferably, the plants will translocate the arsenic from the roots into the shoots (i.e., the aboveground portions of the plant). The rates of accumulation can vary depending on a variety of factors, including the total arsenic concentration, pH, planting density, and fertilizer use. With the teachings provided herein, the skilled artisan can readily select the preferred conditions for a particular application.

Generally, accumulation by the preferred fern plants can be as high as approximately 100-fold or more above the levels present in the environment. The most preferred fern plant members accumulate several percent of arsenic as dry weight of shoot biomass. Shoots can then be harvested. The ability of the plants of the present invention to accumulate arsenic in the shoots is important because the shoots represent the harvestable (i.e., aboveground) biomass. However, any portion of the plant is potentially harvestable. For example, leaves, stems, fronds and roots may be harvested from fern plants.

In addition to highly contaminated soil, fern plant samples were also collected from uncontaminated sites, with arsenic concentrations ranging from approximately 0.5 to approximately 7.6 mg/kg. The arsenic concentrations in the frond (above-ground biomass) of these plants ranged from approximately 12 to approximately 64 mg/kg, with a maximum arsenic enrichment factor of approximately 136. This clearly demonstrates that the fern plants of the subject invention accumulate arsenic from soils containing high as well as low arsenic levels.

Thus, the arsenic enrichment factor of fern plants is observed under natural growing conditions in contaminated as well as uncontaminated soils. The person skilled in the art, having the benefit of the current disclosure could optimize conditions for growth of the plants and uptakes of the pollutants. The uptake reported here is under conditions in the field and could be increased in an appropriately controlled environment such as a greenhouse.

Arsenic concentrations in common plants range from approximately 0.01 to approximately 5 mg/kg, with an average of approximately 2.5 mg/kg. Thus, the fern plants of the subject invention accumulate as much as approximately 3,000 times more arsenic than the average of common plants without suffering from arsenic toxicity. This is extremely unusual for a plant since arsenic has been and still is being used as a herbicide to control weeds.

The fern plants of the subject invention are highly advantageous for use in methods to remove arsenic from contaminated waters. These fern plants also have a relatively large biomass; for example, these fern plants can produce a frond that is approximately 30 to approximately 90 cm in length, with blades of approximately 25 to approximately 60 cm long and approximately 13 to approximately 25 cm wide. Also, fern plants can be easily reproduced in tens of thousands from just one plant. Once planted in an arsenic contaminated soil, the fern plants of the subject invention come back every year because they are perennial plants, i.e., the fern plants can be harvested season after season until the site is cleaned up without reseeding or replanting.

In a specific embodiment, the subject invention concerns an arsenic accumulating *P. vittata*. The arsenic concentration in the water where samples was collected was approximately 10 mg/L, with the highest arsenic concentration in the fronds being approximately 1,666 mg/kg. Hence, the arsenic concentration in the fern can be approximately 167 times greater than that in water. This plant is highly advantageous for extracting arsenic from arsenic contaminated water, including groundwater.

The arsenic accumulating fern plants of the subject invention can be used to remediate tens of thousands of arsenic contaminated waters nationwide and around the world. When the fern plants are harvested, the arsenic, phosphorous or other metal can be recovered or disposed of using methods know to those skilled in the art. The disposed or recovery step may include, for example, microbial treatment, chemical treatment, incineration, treatment with other plants, etc. These methods may further include the use of gasifiers.

The specific applications that this technique can be applied to arsenic contaminated environments include the following:
1. Cleanup arsenic contaminated groundwater or surface water; Arsenic contaminated groundwater or surface water can be pumped up to irrigate the field where the fern plants grow to allow arsenic to be taken up by the fern plants and cleanup the groundwater; Arsenic uptake by the fern is through both roots and fronds.
2. Cleanup waters contaminated with both organics and arsenic. Both Fern plants (uptake arsenic and phosphorus) and poplar trees (help degrade organic contaminants) can be planted in the field to clean up co-contaminated groundwater;
3. Cleanup waters contaminated with both lead and arsenic. Both fern plants (uptake arsenic and phosphorus) and India mustard (uptake lead) can be planted in the field to clean up co-contaminated waters;
4. Treat wastewater. Fern plants can be grown in a field where wastewater can be used for irrigation to remove arsenic from the wastewater;

In a specific embodiment the subject invention concerns a method of phytoremediating contaminated waters comprising cultivating fern plants in the materials containing contaminants under conditions sufficient to permit the fern plants to accumulate contaminants from the materials in the biomass of the fern plants such that the contaminants are at least approximately 100 mk/kg of dry biomass of the fern plants. The fern plants can then be harvested and the contaminants recovered from the biomass. Preferably, the materials are conditioned to an optimized nutrient level to increase plant biomass and contaminants bioavailability. Contaminants include both organic and inorganic pollutants that are of environmental concern and include, but are not limited to, arsenic, phosphorous and other trace elements and heavy metals.

Root Uptake in Plants to Remove Pollutants & Contaminants

EXAMPLE 1

The ability of arsenic accumulation by *P. vittata* over different time periods (1 d, 15 d or 4 weeks) from aqueous solution containing either organic (MMA-monomethylarsonic acid) or inorganic arsenic species (AsIII-arsenite and AsV-arsenate) was demonstrated in Tables 1 and 2. Its effectiveness was compared to *Nephrolepis exaltata*, a non arsenic hyperaccumulator and *Pteris cretica* Mayii, another arsenic hyperaccumulator.

Regardless of arsenic species (AsIII or AsV) and reaction times (1 or 15 d), more arsenic was accumulated in the fronds in *P. vittata*, where more arsenic in the roots for *N. exaltata* (Table 1). Overall, *P. vittata* was much more efficient in arsenic accumulation than *N. exaltata*, with the highest arsenic concentration of 542 mg kg$^{-1}$ being observed in the frond of *P. vittata* receiving 20 mg L$^{-1}$ AsIII for 15 d. In short, *P. vittata* was efficient in removing AsIII or AsV from aqueous solutions.

Regardless of arsenic species (AsIII or MMA) and arsenic concentrations (1 or 10 mg L$^{-1}$), *P. vittata* accumulated more arsenic in the fronds than *N. exaltata* (Table 2), though both are arsenic hyperaccumulators. Typical of arsenic hyperaccumulators, more arsenic was concentrated in the fronds than in the roots.

TABLE 1

As concentrations in *P. vittata* and *N. exaltata* (mg kg$^{-1}$) after growing for 1 or 15 d in a hydroponic solution containing 5 mg L$^{-1}$ AsV or 20 mg L$^{-1}$ AsIII

|  | One day | | 15 days | |
| --- | --- | --- | --- | --- |
|  | Fronds | Roots | Fronds | Roots |
| Control with no As | | | | |
| *P. vittata* | 8.02 ± 2.01* | 0.81 ± 0.34 | 6.77 ± 1.52 | 1.36 ± 0.49 |
| *N. exaltata* | 0.73 ± 0.17 | 1.03 ± 0.25 | 0.85 ± 0.52 | 1.15 ± 0.29 |
| 5 mg/L AsV | | | | |
| *P. vittata* | 38.2 ± 9.8 | 26.5 ± 6.24 | 282 ± 138 | 50.6 ± 21.6 |
| *N. exaltata* | 4.81 ± 2.12 | 25.7 ± 14.4 | 70.6 ± 33.3 | 156 ± 33.9 |
| 20 mg/L AsIII | | | | |
| *P. vittata* | 267 ± 119 | 205 ± 81.2 | 542 ± 67 | 254 ± 97.1 |
| *N. exaltata* | 38.7 ± 36.2 | 128 ± 22.5 | 66.3 ± 12.6 | 144 ± 18.9 |

*mean ± standard deviation of four replications

TABLE 2

As concentrations in *P. vittata* and *P. cretica* Mayii (mg kg$^{-1}$) after growing for four weeks in a hydroponic solution containing 1 or 10 mg L$^{-1}$ AsIII or MMA

| Fern type | MMA (mg/L) | | | As III (mg/L) | | |
|---|---|---|---|---|---|---|
| | 0 | 1 | 10 | 0 | 1 | 10 |
| | Fronds | | | | | |
| *P. vittata* | 10.4aA | 558b A | 1666cA | 10.4aA | 457bA | 1075cA |
| *P. cretica* Mayii | 4.0a B | 4.0a B | 627b B | 4.0a B | 201bB | 249b B |
| | Roots | | | | | |
| *P. vittata* | 3.1a B | 131b A | 357c B | 3.1a B | 82.2bA | 362c B |
| *P. cretica* Mayii | 6.3a B | 69.3bB | 347c B | 6.3a B | 41.9bB | 331c B |

Means on horizontal followed by the same low case letter compare the effect of arsenic concentrations while means on the vertical followed by capital letter compare fern type. Similar letters are not different at P < 0.05

Foliar Application through Live Fern Plants (Fronds) to Remove Pollutants and Contaminants

EXAMPLE 2

Two experiments were conducted to determine the effectiveness of *P. vittata* in taking up arsenic via foliar application. The first experiment used only *P. vittata* on two arsenic species (AsIII and AsV), whereas the second experiment used three fern species (*P. vittata, N. exaltata*, and *Pteris ensiformis*).

In the first experiment, four weeks after sprays with approximately 100 mg L$^{-1}$ AsIII or AsV, *P. vittata* was separated into three parts, leave, stem, and spore and analyzed for total arsenic concentrations. *Pteris vittata* was effective in accumulating arsenic from foliar application (Table 3). Significant arsenic enrichment occurred in the plant, with the highest arsenic concentrations as high as approximately 0.46% in the young leave receiving AsIII, which was approximately 46 times greater than the arsenic solution sprayed on the plant. The young fronds (0–10 weeks old) exhibited greater arsenic absorption than the mature fertile fronds (11–20 weeks old). On an average, the young fronds absorbed approximately 69% more arsenic than the mature fronds. Regardless frond age, more arsenite was absorbed by the plant than arsenate, with an average increase of approximately 7 to approximately 49%.

TABLE 3

Arsenic concentrations (mg kg$^{-1}$) in the fronds of *P. vittata* after spraying with 100 ppm AsIII or AsV

| Plant part | ASIII (NaAsO$_2$) | | AsV (Na$_3$AsO$_4$) | |
|---|---|---|---|---|
| | young | mature | young | mature |
| Leave | 4,610 | 1,100 | 3,200 | 810 |
| Stem | 1,160 | 230 | 960 | 110 |
| Spore | 3,710 | 1,150 | 2,210 | 760 |

In the second experiment, approximately 100 mL of approximately 20 mg L$^{-1}$ arsenic solution (AsIII or AsV) buffered by MES at pH 6 was sprayed to the plants. The spraying was carried out at 8:30 am during 1-h period. The fronds were harvested after approximately 24 hour and analyzed for total As concentrations. During the short period of time (1 d), all three ferns seemed effective in accumulating arsenic, with *P. vittata* being most effective for AsIII and *N. exaltata* for AsV. Though the experiment lasted only for 1 d, toxicity symptoms were observed in *N. exaltata* and *P. ensiformis*, indicating *P. vittata* was not only effective in accumulating arsenic, but also effective detoxifying arsenic once inside the plant. Detoxifying results were shown since *P. vittata* showed no toxicity while *N. exaltata* did.

TABLE 4

Arsenic concentration (mg kg$^{-1}$) in the fronds of three fern species.

| Treatments | *P. vittata* | *N. exaltata* | *P. ensiformis* |
|---|---|---|---|
| Control | 1.07 (0.16)* | 0.99 (0.66) | 1.92 (0.50) |
| As(III) | 113 (29.3) | 91.9 (19.4) | 74.9 (20.8) |
| As(V) | 98.0 (16.9) | 128 (35.3) | 70.9 (12.2) |

*The data in parentheses are standard error of the mean from four replicates.

Excised Fern Plant Portions (i.e. Leaflets) to Remove Pollutants and Contaminants

EXAMPLE 3

Two experiments were conducted to determine the effectiveness of excised *P. vittata* in taking up arsenic from aqueous solution. In the first experiment, excised *P. vittata* leaflets were soaked in approximately 50 mg L$^{-1}$ AsIII, AsV or MMA (monomethylarsonic acid) in the presence or absence of P, whereas in the second experiment excised leaflets from three fern species (*P. vittata, N. exaltata*, and *P. ensiformis*) were soaked in approximately 20 mg L$^{-1}$ AsIII or AsV.

In the first experiment, the excised leaflets of *P. vittata* were soaked in a solution containing approximately 50 mg L$^{-1}$ AsIII, AsV, or MMA and approximately 0 or approximately 16 mg L$^{-1}$ P for 1-d (Table 5). The leaflets absorbed significant amounts of As within a day of exposing to arsenic, with the highest arsenic concentration being observed at approximately 4,066 mg kg$^{-1}$ in the leaflets exposed to AsIII in the presence of P. The presence of P only significantly reduced AsV uptake by the leaflets, with the order being AsIII>AsV>MMA in the presence of P and AsIII>MMA>AsV in the absence of P, suggesting that AsV was most likely taken up by the P carriers.

TABLE 5

Arsenic concentrations (mg kg$^{-1}$) in the leaflets after soaking for 1 d in aqueous solution containing 50 mg L$^{-1}$ AsIII, AsV or MMA

| Different arsenic species | In the absence of P | In the presence of P |
|---|---|---|
| Control | 799 | 633 |
| AsIII | 3,473 | 4,066 |
| AsV | 2,213 | 1,698 |
| MMA | 1,961 | 2,233 |

In the second experiment, the excised leaflets of *P. vittata, N. exaltata* and *P. ensiformis* were exposed to approximately 20 mg L$^{-1}$ AsIII or AsV, which was buffered by MES at pH 6, for 1-d (Table 6). After 1 d, the leaflets were first rinsing in ice-cold phosphate buffer containing approximately 1 mM Na$_2$HPO$_4$, approximately 10 mM MES and approximately 0.5 mM Ca(NO$_3$)$_2$ to ensure desorption of arsenic from material surface and then washed with tap water followed by deionized water. The leaflets were dried at approximately 65° C., ground, and analyzed total As. Regardless of arsenic species, excised *P. vittata* was the most effective in taking up both AsIII and AsV, with AsIII being more effective in AsV (Table 6). *P. vittata* took up approximately 353 mg kg$^{-1}$ AsIII, which was approximately 2.2 and approximately 4.4 times more than that of *N. exaltata* and *P. ensiformis*, respectively. In term of AsV, *P. vittata* took up approximately 142 mg kg$^{-1}$, which was approximately 40% less than that of AsIII.

TABLE 6

Arsenic concentrations (mg kg$^{-1}$) in the leaflets after soaking for 1 d in aqueous solution containing 50 mg L$^{-1}$ AsIII, AsV or MMA

| Treatments | *P. vittata* | *N. exaltata* | *P. ensiformis* |
|---|---|---|---|
| Control | 4.75 (0.50)* | 1.34 (0.47) | 0.20 (0.34) |
| AsIII | 353 (4.97) | 160 (1.78) | 80.5 (2.55) |
| AsV | 142 (6.76) | 53.3 (0.86) | 40.0 (2.25) |

*The data in parentheses are standard error of the mean from three replicates.

Other excised plant parts, such as stems, and the like, would also absorb arsenic. All types of other acqueous solution water environments, such as but not limited to wastewater, ground water, surface water, and the like, can use the invention. The invention can work as long as the excised plant parts, such as the leaflets make direct contact with acqueous environments.

Ground Fern Biomass to Remove Pollutants & Contaminants

EXAMPLE 4

Two experiments were conducted to determine the effectiveness of ground biomass of *P. vittata* in taking up arsenic from aqueous solution. In the first experiment, ground fresh (biomass without drying), air-dry (biomass was dried at room temperature for 3-d), and freeze-dry (biomass was dried using a freeze drier for 24-h) fronds of *P. vittata* and *N. exaltata* were mixed with arsenic, whereas in the second experiment ground fresh and air-dry fronds from three fern species (*P. vittata*, *N. exaltata*, and *P. ensiformis*) were reacted with arsenic.

In the first experiment, the biomass of *P. vittata* and *N. exaltata* of approximately 0.2 g was added to approximately 30 mL solutions containing approximately 1 or approximately 10 mg L$^{-1}$ AsIII or AsV and shaken on a mechanical shaker for approximately 12 hours at room temperature. The samples were then centrifuged at approximately 3,500 rpm for approximately 15 minutes and the settled phytomass was analyzed for total arsenic.

The smaller the ground parts, the potentially better the results.

Regardless of arsenic concentrations (approximately 1 or approximately 10 mg L$^{-1}$) or arsenic species (AsIII or AsV), the biomass of *P. vittata* was more effective in absorbing arsenic from solution than that of *N. exaltata* (Table 7). Among the three biomass, fresh biomass was the most effective followed by air dry biomass and freeze dry biomass. Among the two arsenic species, the fern biomass was more effective in taking AsIII than AsV.

TABLE 7

Arsenic concentrations (mg kg$^{-1}$) in ground leaflets of *P. vittata* after mixing with solution containing 1 or 10 mg L$^{-1}$ AsIII or AsV for 12 hours

| | AsIII | | AsV | |
|---|---|---|---|---|
| Biomass | *P. vittata* | *N. exaltata* | *P. vittata* | *N. exaltata* |
| | Solution As = 1 mg L$^{-1}$ | | | |
| Fresh | 0.34 | 0.29 | 0.33 | 0.12 |
| Air-dry | 0.32 | 0.19 | 0.14 | 0.08 |
| Freeze-dry | 0.13 | 0.08 | 0.06 | 0.08 |
| | Solution As = 10 mg L$^{-1}$ | | | |
| Fresh | 11.7 | 11.1 | 3.40 | 0.53 |
| Air-dry | 8.47 | 0.47 | 2.77 | 0.36 |
| Freeze-dry | 5.18 | 0.34 | 1.19 | 0.26 |

In the second experiment, biomass of approximately 0.2 g air-dry or approximately 1 g fresh fronds was mixed with approximately 50 mL solution containing approximately 20 mg L$^{-1}$ AsIII or AsV on a shaker for 1-d at room temperature. The slurry was filtered by vacuum and the plant biomass was washed with deionized water for three times, oven dried at approximately 45° C. for 2-d and analyzed for total arsenic. Similar to Table 7, fresh fern biomass was more effective in taking up arsenic than air-dry biomass, but no significant differences were observed among three fern species in their ability to absorb arsenic (Table 8).

TABLE 8

Arsenic concentrations (mg kg$^{-1}$) in ground fresh or air-dry fronds of three fern species after reacting with 20 mg L$^{-1}$ As for 1 d.

| Treatments | *P. vittata* | *N. exaltata* | *P. ensiformis* |
|---|---|---|---|
| | Fresh biomass | | |
| As(III) | 40.3 (6.36)* | 95.8 (7.11) | 54.6 (15.3) |
| As(V) | 24.1 (4.24) | 65.7 (25.0) | 48.4 (14.7) |
| | Air-dry biomass | | |
| As(III) | 16.9 (5.75) | 14.7 (4.34) | 14.9 (3.71) |
| As(V) | 19.8 (1.4) | 14.1 (3.54) | 7.22 (6.13) |

*The data in parentheses are standard error of the mean from three replicates.

While ground plant parts, such as fronds are preferred, other plant parts can be ground, and the ground parts can be placed in similar water acqueous environments as the excised plant parts described above.

The invention embodiments can remove pollutants and contaminants from various environments such as but not limited to water, aqueous solutions, wetlands, soil, air and surrounding atmosphere environment contaminated by herbicide sprays, and the like.

Although the invention embodiments have been described as being used separately, the invention can be practiced by combining any one of the embodiments with another. For example, root uptake of contaminants can be combined with foliar application, and the like.

While the invention has been described, disclosed, illustrated and shown in various terms of certain embodiments or modifications which it has presumed in practice, the scope of the invention is not intended to be, nor should it be deemed to be limited thereby and such other modifications or embodiments as may be suggested by the teachings herein are particularly reserved especially as they fall within the breadth and scope of the claims here appended.

We claim:

1. A process for removing a pollutant through a foliar application, comprising the steps of:
    growing a fern plant selected from the group consisting of *Pteridaceae, Adiantaceae, Aspleniaceae, Dryopteridaceae*, and *Oleandraceae*, in an environment site containing the pollutant; and
    removing a portion of the pollutant by phytoremediation through contact with a live part of the fern plant.

2. The process of claim 1, wherein the environment site includes: a contaminated aqueous solution.

3. The process of claim 1, wherein the environment site includes: a contaminated water selected from at least one of: ground water and surface water.

4. The process of claim 1, wherein the environment site includes: a contaminated wetlands.

5. The process of claim 1, wherein the environment sites includes: a contaminated soil.

6. The process of claim 1, wherein the environment site includes: a contaminated air.

7. The process of claim 6, further includes the step of contaminating the air environment by spraying the pollutant onto the plant part.

8. The process of claim 7, wherein the pollutant includes: arsenite.

9. The process of claim 7, wherein the pollutant includes: arsenate.

10. The process of claim 1, wherein the live plant part includes: a live leaf portion.

11. The process of claim 10, wherein the pollutant portion includes approximately 110 to approximately 4610 mg/kg of arsenic concentration per live leaf portion.

12. The process of claim 1, wherein the live plant part includes: a live stem portion.

13. The process of claim 12, wherein the pollutant portion includes approximately 110 to approximately 1,160 mg/kg of arsenic concentration per live stem portion.

14. The process of claim 1, wherein the live plant part includes: a live spore portion.

15. The process of claim 1, wherein the pollutant portion includes approximately 760 to approximately 3,710 mg/kg of arsenic concentration per live spore portion.

16. The process, according to claim 1, wherein said fern plant is of the family *Pteridaceae*.

17. The process, according to claim 1, wherein said fern plant is of the family *Adiantaceae*.

18. The process, according to claim 1, wherein said fern plant is *Adiantum raddianum*.

19. The process, according to claim 1, wherein said fern plant is of the genus *Pteris*.

20. The process, according to claim 1, wherein said fern plant is *Pteris cretica* parkerii.

21. The process, according to claim 1, wherein said fern plant is a *Pteris cretica* albo-lineata.

22. The process, according to claim 1, wherein said fern plant is a *Pteris cretica* mayii.

23. The process, according to claim 1, wherein said fern plant is a *Pteris vittata*.

24. The process, according to claim 1, wherein up to approximately 100% of arsenic in the environment site is being removed.

25. A process for removing a pollutant through an excised plant part, comprising:
    excising a live part of a fern plant selected from the group consisting of *Pteridaceae, Adiantaceae, Aspleniaceae, Dryopteridaceae*, and *Oleandraceae;*
    applying the excised live plant part to an environment site containing the pollutant; and
    removing a portion of the pollutant by phytoremediation through contact with the excised live plant part.

26. The process of claim 25, wherein the excised plant part includes: an excised leaflet.

27. The process of claim 25, wherein the environment site includes: a contaminated aqueous solution.

28. The process of claim 25, wherein the environment site includes: a contaminated ground water or contaminated surface water.

29. The process of claim 25, wherein the environment site includes: a contaminated wetlands.

30. The process of claim 25, wherein the environment sites includes: a contaminated soil.

31. The process of claim 25, wherein the environment site includes: a contaminated air.

32. The process of claim 31, wherein the contaminated air includes: the step of
    contaminating the air environment by spraying the pollutant onto the excised live plant part.

33. The process of claim 25, wherein the pollutant includes: arsenite.

34. The process of claim 25, wherein the pollutant includes: arsenate.

35. The process of claim 25, wherein the pollutant portion includes: approximately 1,961 to approximately 4,066 mg/kg of arsenic per plant part.

36. The process, according to claim 25, wherein said fern plant is of the family *Pteridaceae*.

37. The process, according to claim 25, wherein said fern plant is of the family *Adiantaceae*.

38. The process, according to claim 25, wherein said fern plant is *Adiantum raddianum*.

39. The process, according to claim 25, wherein said fern plant is of the genus *Pteris*.

40. The process, according to claim 25, wherein said fern plant is *Pteris cretica* parkerii.

41. The process, according to claim 25, wherein said fern plant is a *Pteris cretica* albo-lineata.

42. The process, according to claim 25, wherein said fern plant is a *Pteris cretica* mayii.

43. The process, according to claim 25, wherein said fern plant is a *Pteris vittata*.

44. The process, according to claim 25, wherein up to approximately 100% of arsenic in the environment site is being removed.

45. A process for removing a pollutant through ground up plant part, comprising:
    excising a live part of a fern plant selected from the group consisting of *Pteridaceae, Adiantaceae, Aspleniaceae, Dryopteridaceae*, and *Oleandraceae;*
    grounding the excised plant part into ground biomass; and
    removing a portion of the pollutant by phytoremediation through contact with the ground biomass.

46. The process of claim 45, wherein the plant part includes: a leaflet.

47. The process of claim 45, wherein the ground up parts of the biomass is: fresh ground up parts of the biomass.

48. The process of claim 45, wherein the ground biomass is: air-dried ground up parts of the biomass.

49. The process of claim 45, wherein the ground biomass is: freeze dried ground up parts of the biomass.

50. The process of claim 45, wherein the pollutant includes: arsenite.

51. The process of claim 45, wherein the pollutant includes: arsenate.

* * * * *